United States Patent [19]

Rimbaud

[11] 3,930,499
[45] Jan. 6, 1976

[54] HYPODERMIC SYRINGE WITH PARTS DISPOSABLE AFTER USE

[75] Inventor: Henri Rimbaud, Paris, France

[73] Assignee: Laboratoire S P A D, Quetingny-les-Dijon, France

[22] Filed: May 31, 1974

[21] Appl. No.: 475,146

Related U.S. Application Data

[62] Division of Ser. No. 308,844, Nov. 22, 1972, Pat. No. 3,878,846.

[52] U.S. Cl. ............ 128/218 DA; 128/272; 206/365
[51] Int. Cl.² ............................................ A61M 5/00
[58] Field of Search ... 128/215, 216, 218 P, 218 M, 128/218 DA, 218 R, 218 D, 218 NV, 218 N, 220, 221, 272; 206/438, 364–370

[56] References Cited
UNITED STATES PATENTS

| | | | |
|---|---|---|---|
| 2,728,341 | 12/1955 | Roehr | 128/218 D |
| 2,847,996 | 8/1958 | Cohen et al. | 128/218 M |
| 2,869,542 | 1/1959 | Orsten et al. | 128/218 D |
| 3,084,688 | 4/1963 | McConnaughey | 128/218 NV |
| 3,110,309 | 11/1963 | Higgins | 128/218 D |
| 3,433,216 | 3/1969 | Mattson | 128/DIG. 5 |
| 3,677,247 | 7/1972 | Brown | 128/221 |
| 3,742,948 | 7/1973 | Post et al. | 128/218 D |
| 3,820,652 | 6/1974 | Thackston | 128/221 |

FOREIGN PATENTS OR APPLICATIONS

| | | | |
|---|---|---|---|
| 66,437 | 10/1956 | France | 128/218 D |
| 876,742 | 7/1949 | Germany | 128/215 |
| 1,491,663 | 8/1969 | Germany | 128/218 R |
| 1,579,072 | 7/1969 | France | 128/218 D |
| 728,253 | 4/1955 | United Kingdom | 128/218 N |

*Primary Examiner*—Robert W. Michell
*Assistant Examiner*—Henry S. Layton
*Attorney, Agent, or Firm*—Haseltine, Lake & Waters

[57] ABSTRACT

A hypodermic syringe comprising a head, a rod slidingly mounted in the head and gripping elements fixed to the head and to the exterior free end of the rod. The gripping element fixed to the body is mounted on the latter adjustably in the longitudinal direction with respect to the gripping element fixed to the exterior end of the rod.

6 Claims, 8 Drawing Figures

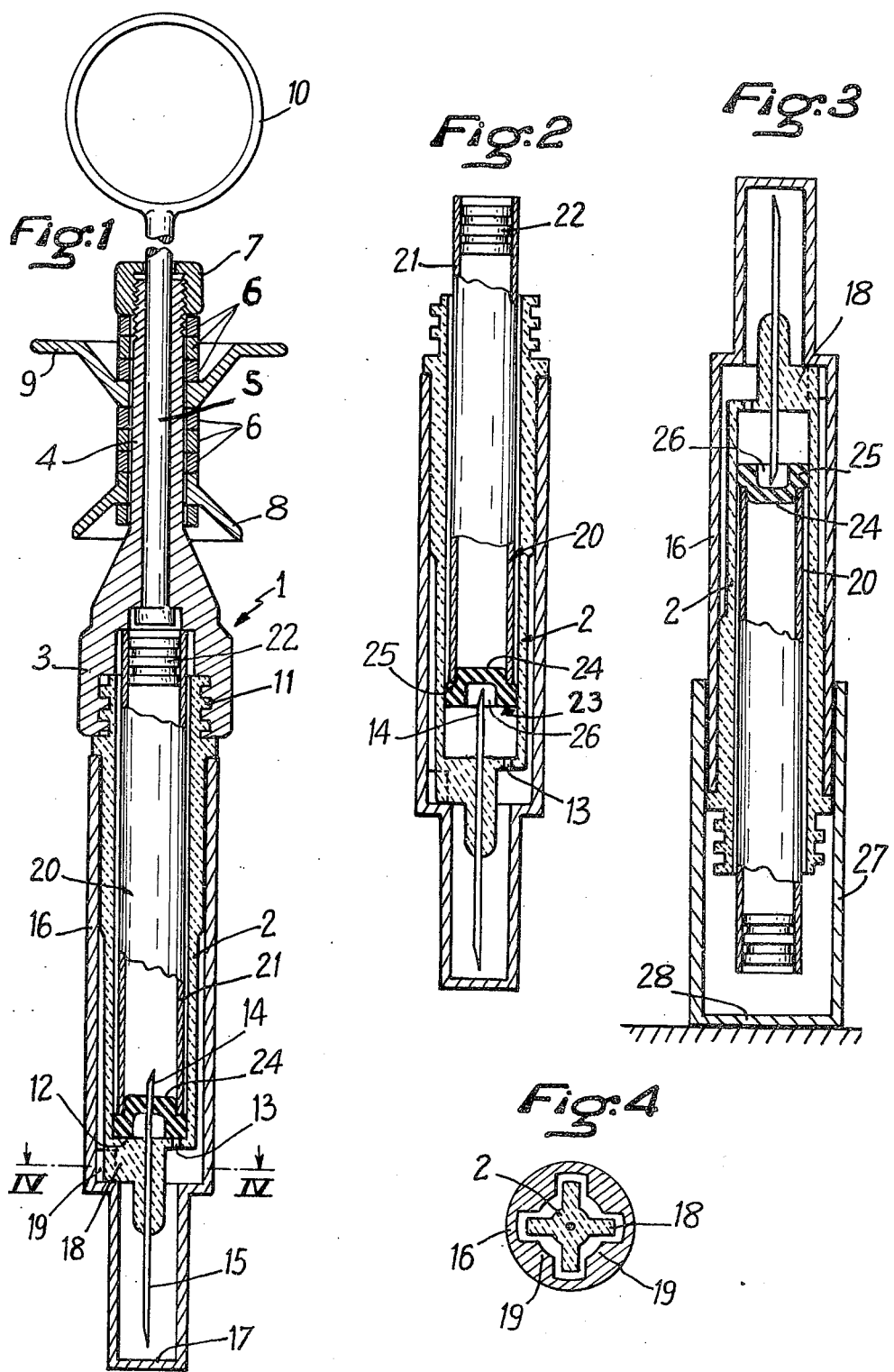

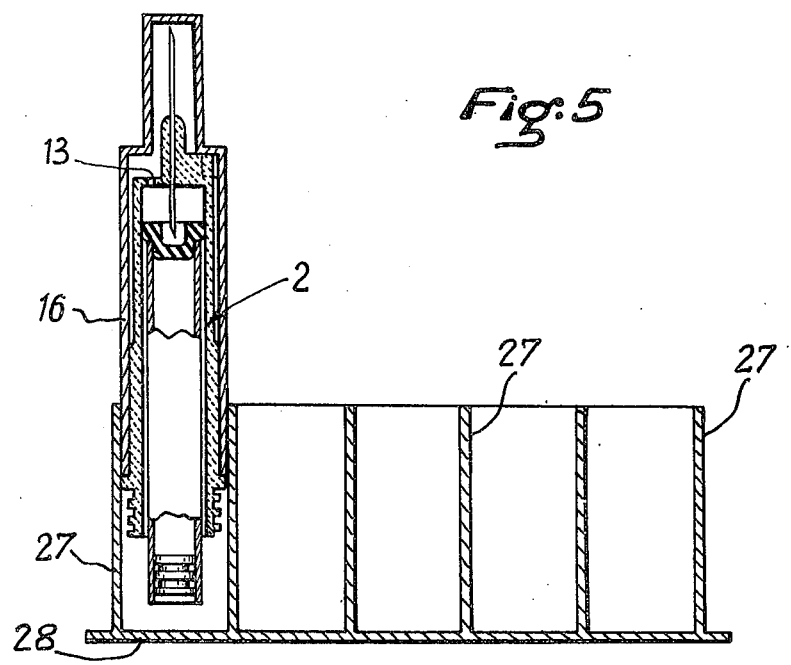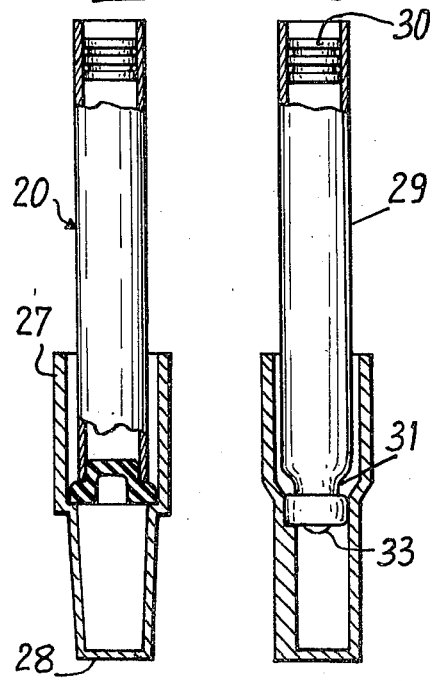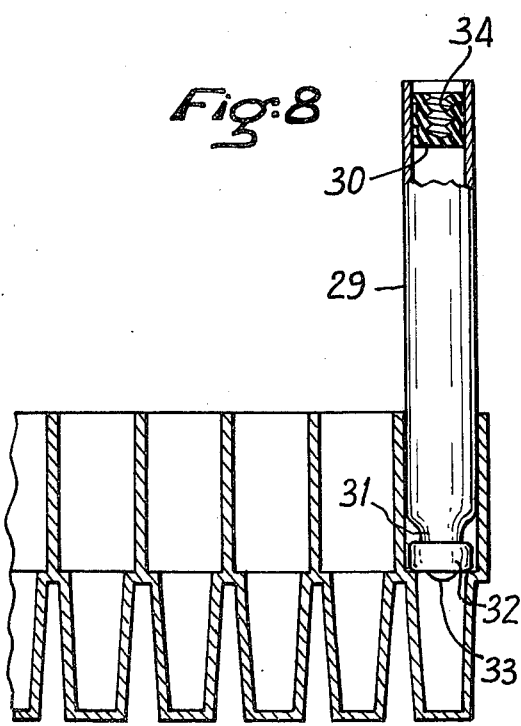

HYPODERMIC SYRINGE WITH PARTS DISPOSABLE AFTER USE

CROSS-RELATED APPLICATION

This Application is a division of copending Application Ser. No. 308,844, filed Nov. 22, 1972 now U.S. Pat. No. 3,878,846.

BACKGROUND OF THE INVENTION

1. Field of the Invention

This invention relates to hypodermic syringes and in particular to adjustable gripping elements therefor.

2. Description of the Prior Art and Objects of the Invention

Syringes, particularly those used by dentists, are known which comprise a syringe head having fixed gripping elements by which the syringe is held and anaesthetic is operatively supplied therefrom for the purpose of an injection.

An object of the present invention is to provide a syringe comprising a head which is suitable for all users irrespective of the size of their hand.

A particular object of the invention is to provide a syringe having adjustable gripping means to accommodate hands of different size.

SUMMARY OF THE INVENTION

According to the invention there is provided a hypodermic syringe comprising a syringe head, a rod slidingly mounted in the head for axial movement therein and gripping elements fixed to the head and to the exterior free end of the rod, the gripping element fixed to the head being mounted on the latter adjustably in the longitudinal direction with respect to the gripping element fixed to the exterior end of the rod.

Suitably the head comprises a sleeve in which the rod slides, rings stacked on the said sleeve, locking means for locking the rings in the axial direction fitted at one end of the sleeve, the gripping element associated with the head being constituted by a disc interposed between two rings of the set of rings, the locking means being demountable to enable the disc to be interposed between any two other rings.

In another embodiment, a second disc is interposed between the rings at a point remote from the first disc. The two discs each may have a frustoconical profile, one being flared in the opposite direction.

Alternatively, the gripping element may comprise two spaced double lugs interposed between the stacked rings and clamped along a sleeve in which the rod slides. As a further alternative the gripping elements may comprise two spaced double lugs each fitted with a locking screw and mounted slidably in the axial direction along a sleeve in which the rod slides.

The head is preferably fitted with a screwthread for attachment to the body, the body suitably being of moulded material and in the form of a hollow tube having an open end provided with a screwthread complementary to that of the head.

BRIEF DESCRIPTION OF THE DRAWING

FIG. 1 is a vertical cross-section through a syringe fitted with a syringe body containing an anaesthetic cartridge and shielded by a protective case;

FIG. 2 is a vertical cross-section through a syringe body containing a cartridge prior to its assembly with the head of a syringe;

FIG. 3 is a section similar to FIG. 2, the case being arrange in a protective support;

FIG. 4 is a section along the line IV—IV of FIG. 1;

FIG. 5 is a cross-section through a support with multiple cells for cases containing a syringe body and a cartridge with a syringe and a cartridge disposed in one cell;

FIGS. 6 and 7 are cross-section elevations showing a cartridge according to the invention and a conventional cartridge each arranged on an individual support; and FIG. 8 is a cross-sectional elevation of a support with multiple cells for cartridges with a conventional cartridge provided with a piston with screwthread shown part in section.

DESCRIPTION OF THE PREFERRED EMBODIMENTS

Referring to the drawings, FIG. 1 shows a hypodermic syringe with a syringe head designated by the reference 1, and a syringe body designated by the reference 2.

Only the head 1 is the permanent element, made of metal, which does not require to be sterilized and which the user may retain. The head comprises a tip 3 having at one end an internal screwthread and prolonged at the opposite end by a sleeve 4 in which a rod 5 slides.

Upon the sleeve 4 there are stacked rings 6 clamped by a nut 7 which is screwed to the extreme terminal part of the sleeve.

Between the rings there are interposed two spaced discs 8 and 9 which have overall a frustoconcial profile, one being flared towards the free end of the rod and the other in the opposite direction.

The rod 5 is provided at its end with a ring 10 large enough for the passage of a thumb.

The disc 9 and the ring 10 constitute a set of gripping elements which are used to give an injection, the index and second fingers being braced against the disc 9 while the thumb is engaged in the ring 10.

The gripping element fixed to the tip, i.e. the disc 9, can easily be moved along the sleeve 4 in order to regulate the distance of said elements as a function of the size of the operator's hand.

The disc 8, likewise adjustable in position, enables the syringe to be grasped more easily between the index and second fingers which may be slid between the two discs 8 and 9.

The syringe body 2 may be fabricated of moulded material, for example, of injection moulded plastics. It is supplied in sterile condition and intended to be disposable after use. It is constituted by a hollow tube having an open end fitted with a screwthread 11 complementary to that of the tip 3. The opposite end is closed by a transverse blocking wall 12 pierced with a rather small off-center hole 13.

In the wall 12, which is provided with a central reinforcement for this purpose, there is anchored a double needle which has an internally protruding part 14 and an externally protruding part 15.

The body 2 is protected for its delivery and its storage inside a case 16. The latter is a hollow tubular element moulded of plastic material, preferably of polyethylene, which fits snugly and air-tight upon the external face of the body. One end of the element is blocked by a solid wall 17. Its length is such that when the body is introduced into it, the screwthread 11 remains free whereas the entire remainder of the body including the needle 15 is shielded fluid tightly.

In the region of the reinforcement which retains the double needle, the body 2 is fitted externally with at least one stop 18. In this example, as FIG. 4 shows, there are four stops 18. The case 16 is fitted internally with four stops 19 situate in the same sectional plane as the stops 18.

The stops 18 and 19 come into contact as a result of a relative movement in rotation of the case and of the body. It is therefore possible to screw the body 2 onto the tip 3 by holding only the case 16, without having to disengage the body from it.

The same fixation in rotation could be achieved by giving to the body 2 and to the case 16, or to a portion of these parts, a cross-sectional profile which is not of revolution about their common axis.

Referring to FIGS. 2 and 3, these show in detail cartridges containing an anaesthetic, which are generally supplied in sterile condition, arranged inside the body 2.

The cartridge of the invention, designated by the reference numeral 20, comprises a tube 21 of constant section fitted at one end with a fluid piston 22 displaceable inside the tube and provided at its opposite end with a plug 23 of elastic material, for example of rubber.

The plug 23 comprises a first part 24 fitted in the interior of the tube 21 and a second part 25 exterior to the tube 21. Said second part 25 covers the extreme portion of the tube 21 and it has externally a dimension, for example a diameter, which is greater than the interior dimension of the body of the syringe.

A blind cavity 26 is provided in the plug 23; it opens into the exterior extreme face of the second part 25 and extends inside the first part 24 of the said plug. Thus, the walls of the first part 24 are reduced in thickness and they are capable of being crushed elastically upon themselves. With a plug fabricated of a sufficiently flexible elastomer, it would not be necessary to reduce in thickness the walls of the first part 24 to obtain an elastic crushing of this part of the plug.

When a cartridge 20 is introduced into the interior of the body 2, the plug 23 leading, by virtue of the friction of the latter against the internal face of the body, the said cartridge remains in the position in which it is placed.

Before the syringe body is assembled upon the syringe head, the case-body-cartridge assembly is in the state visible in FIG. 2. The cartridge 20 is anchored in the body 2 by virtue of the friction of the plug 23, at such a depth that the latter is not perforated by the interior part 14 of the needle.

In order to supply and maintain the said assembly in sterile condition, according to the invention a support 27 is provided for use individually (FIG. 3) or grouped with others so as to constitute a multiple celled support (FIG. 5).

Each support 28 comprises a base 27 upon which it rests and a wall (FIG. 3) or a plurality of mutually adjacent walls (FIG. 5) which rise from the base and limit one or more cells. The latter are adapted to receive with friction and air-tightly an extreme part of a case containing a body and a cartridge or a body alone.

It is possible to provide supports of smaller size adapted to receive in the same fluid tight manner an extreme part of a cartridge according to the invention (FIG. 6) or a conventional cartridge (FIGS. 7 and 8) either individually or in a group.

The cartridges 20 of the invention and the conventional cartridges are introduced into their supports by their plug or by their crimped joint which must be pierced by the interior needle 14 of the syringe body.

An internal shoulder or stop limits to an appropriate value the insertion of the cartridges into their supports; the same may apply to the cases.

When the cases are fabricated of polyethylene, the supports are preferably made of polystyrene, since the contact of these two materials achieves a better fluid tight seal than the contact of identical materials. Furthermore, polyethylene is permeable to ethylene oxide whereas polystyrene is not. Therefore the interior of a complete block like those in FIG. 3 or in FIG. 5 can be sterilized before their assembly, by placing them in an atmosphere of ethylene oxide under pressure. The gas passes through the wall of the case 16, spreads in the support 27 and in the body 2 through the lower aperture and through the upper aperture 13.

The supports and the blocks of supports of the invention ensure durably and with certainty the sterility on the one hand of the syringe body and the cartridge, and on the other hand of the plug which will be pierced by the needle.

A single movement of the hand is sufficient to take a case-body-cartridge assembly or a cartridge alone without having to undertake an additional sterilization.

When an assembly in the state visible in FIG. 2 has been grasped and withdrawn from its support, the body 2 is screwed into the tip 3 as stated hereinbefore.

During the screwing, the cartridge 20 is constrained to descend into the body of the syringe and the plug 23 is pierced by the internal needle 14.

At the end of stroke of the screwing, the extreme portion of the tube 21 crushes the external part 25 of the plug against the internal face of the wall 12. Said crushing ensures fluid tightness at the end of the cartridge and of the body.

The case is then withdrawn by a simple sliding movement along the body 2, and the syringe is ready for use.

When a force is exerted upon the rod 5, the piston 22 is thrust into the cartridge; the liquid which it contains is placed under pressure and the interior part 24 of the plug which receives the said pressure is elastically compressed, diminishing in height. If at this moment the force exerted upon the rod 5 is relaxed, then the interior part 24 of the plug expands, repels the liquid of the cartridge and thus produces a suction. The latter is weak but it is sufficient to verify whether the tip of the needle 15 has stopped in a blood vessel.

To perform a second injection with the same syringe body, the case 16 is taken once more, the body 2 is unscrewed, the empty cartridge is thrown away and is replaced by a full cartridge which is extracted from its support and which is introduced into the body 2, as in FIG. 2, without having to grasp it by the plug which must remain sterile.

In order to dispose of the body of the syringe when it has been unscrewed from the tip by means of the case 16, the latter is not withdrawn. In this manner the point 15 which could wound or contaminate remains enclosed in the case.

The invention permits the use of a conventional cartridge 29 which has, at its end opposite to the piston 30, a shrinkage 31; the latter serves to fit a crimping capsule 32 with a central orifice which maintains in position a fluid tight seal 33. Some pistons 30 have a screwthreaded blind hole 34.

In this case the free end of the rod 5 is screwthreaded like the hole 34 and the rod itself is anchored in rotation inside the sleeve 4 by virtue of a groove and of a lug (not shown). The internal face of the syringe body is equipped with longitudinal lamellae (not shown) which oppose the rotation of the cartridge 29 and which also brake its translation inside the body.

During the screwing of the tip 3 and of the body 2, the rod 5 is screwed in the plug 30. This permits the verifying suction discussed hereinbefore to be effected by a traction applied to the rod 5.

The present invention also embraces those modifications and variants which do not depart from its ambit or from its spirit. The syringe illustrated and described is adapted for use by dentists, but it will be apparent that it is also suitable for other uses.

For example, the use of a double claw or of a double lug equipped with a locking screw will be considered an equivalent means to the discs 8, 9 and to the rings 6. The said screws serve to anchor the lug at the desired point along the sleeve 4.

What is claimed is:

1. A syringe comprising a syringe body delivered sterile ready for use to be discarded after a single usage, said syringe body having one extremity with connection means thereat for attachment to a syringe head, a needle mounted at the opposite extremity of said body, said needle extending partially into the interior of the body and partially externally thereof, said syringe body being delivered in combination with a cartridge of injectible fluid frictionally held in said body and including at one extremity thereof a closure non-slidably fitted in said cartridge and placed in facing relation with the part of the needle extending into the interior of the body, said cartridge including, at the other extremity thereof, a piston which is slidable in the cartridge, a removable case mounted on the body and covering a portion thereof and the externally extending portion of the needle while leaving said connection means exposed, means coupling said case and body for common rotation, and a detachable support mounted on the case and covering the rest of said body, said support being separable from the case and thus disengaged from the connection means.

2. The combination as claimed in claim 1 wherein said opposite extremity of said syringe body is provided with an aperture separate from said needle.

3. The combination as claimed in claim 1 wherein said cartridge comprises a tube of constant section fitted with said piston in fluid-tight relation, said closure at the opposite end comprising a plug of elastic material including a first part fitting into the interior of the tube and a second part external to the tube and having an external dimension greater than the internal dimension of the syringe body so that the plug exerts a frictional force against the internal face of the syringe body and opposes free sliding of the cartridge in the body.

4. The combination as claimed in claim 3 wherein said first part of the plug fitted into the interior of the tube of the cartridge has thin walls such that said first part is deformed elastically by the pressure of the liquid in the course of injection.

5. The combination as claimed in claim 4 wherein said plug has a blind cavity which opens at the exterior extreme face of said second part of said plug and which extends inside said first part of the plug.

6. The combination comprising
a syringe head adapted to be retained by the user for permanent use without sterilization,
a syringe body delivered in sterile state to the user said syringe head including at one extremity thereof connection means for attachment to said syringe body, said syringe body having at one extremity thereof means for complementary connection to the connection means of the syringe head, said syringe body being furnished to the user for attachment to the syringe head and comprising before its fixation to said syringe head, an injection needle situated at the extremity opposite to that of the complimentary connection means, said needle extending partially into the interior of the body and partially externally thereof, a cartridge of injectible fluid frictionally mounted in said body and having at one extremity thereof a closure non-slidably fitted in said cartridge and placed in facing relation with the part of the needle extending into the interior of the body, said cartridge including, at the other extremity thereof, a piston slidably mounted in the cartridge,
a removable case mounted on the body and covering one portion thereof and the externally extending portion of the needle while leaving said complimentary connection means exposed,
means coupling said body and case and permitting manual manipulation of the case, without contact of the fingers of the user with said body, said cartridge and said needle, for assembly of the complimentary connection means of said syringe body with the connection means of said syringe head,
and a detachable support mounted on the case and covering the rest of said syringe body, said support being separable from the case thus exposing the complimentary connection means for successive attachment of sterile syringe bodies with the same syringe head.

* * * * *